United States Patent [19]

Langer et al.

[11] Patent Number: 4,753,652

[45] Date of Patent: Jun. 28, 1988

[54] BIOMATERIAL IMPLANTS WHICH RESIST CALCIFICATION

[75] Inventors: Robert Langer, Somerville; Robert J. Levy, Newton, both of Mass.

[73] Assignee: Children's Medical Center Corporation, Boston, Mass.

[21] Appl. No.: 939,275

[22] Filed: Dec. 10, 1986

Related U.S. Application Data

[63] Continuation of Ser. No. 607,191, May 4, 1984, abandoned.

[51] Int. Cl.⁴ .......................... A61F 2/00; A61F 2/26; A61F 2/29
[52] U.S. Cl. .......................................... 623/1; 623/8; 623/12; 623/22; 8/94.11; 8/404
[58] Field of Search .................... 8/94.11, 404; 623/1, 623/8, 12, 22; 514/964; 424/78

[56] References Cited

U.S. PATENT DOCUMENTS

| | | | |
|---|---|---|---|
| 4,310,397 | 1/1982 | Kaetsu et al. | 424/78 |
| 4,343,789 | 8/1982 | Kawata et al. | 424/78 |
| 4,378,224 | 3/1983 | Nimni et al. | 8/94 |
| 4,402,697 | 9/1983 | Pollock et al. | 8/94 |
| 4,419,340 | 12/1983 | Yolles | 424/78 |
| 4,481,009 | 11/1984 | Nashef | 8/94.11 |
| 4,554,155 | 11/1985 | Allan et al. | 424/78 |

OTHER PUBLICATIONS

Henry et al., *J. Clin. Invest.* 68:1366–1369, 1981.
Wartman et al., *J. Atheroseler, Res.* 7: 331–341, 1967.
Kramsch et al., *Circ. Res.* 42: 562–571, 1978.
Potokar & Schmidt-Dunker, "The Inhibitory Effect of New Diphosphonic Acids on Aortic and Kidney Calcification in Vivo", *Atherosclerosis*, 30 (1978) pp. 313–320.
Levy, et al., "Prevention of Bioprosthetic Heart Valve Calcification", *Abstracts of the 56th Scientific Sessions.*
Olanoff et al., "Sustained Release of Gentamicin from Prosthetic Heart Valves," *Trans. Am. Soc. Artif. Intern. Organs*, 25:334–338, (1979).

Primary Examiner—John Kight
Assistant Examiner—Kriellion Morgan

[57] ABSTRACT

A biomaterial implant into which is incorporated a sustained release polymer containing an anticalcium agent.

33 Claims, 2 Drawing Sheets

BIOMATERIAL IMPLANTS WHICH RESIST CALCIFICATION

This is a continuation of co-pending application Ser. No. 607,191 filed on May 4, 1984, now abandoned.

BACKGROUND OF THE INVENTION

This invention relates to the inhibition of calcification of biomaterial implants.

Pathologic calcification represents the end stage of virtually all acquired cardiovascular disease and complicates a wide variety of biomaterial implants. Typically, the term pathologic calcification refers to the deposition of calcium phosphate mineral salts in association with a disease process. Calcification of bioprosthetic cardiac valves (BCV) represents the most common cause of the clinical failure of these devices.

Nimni et al. U.S. Pat. No. 4,378,224 describes inhibiting calcification of glutaraldehyde-stabilized bioprosthetics by treating them with amino group-containing compounds such as diphosphonates, or with calcium chelating agents prior to implantation.

SUMMARY OF THE INVENTION

In general, the invention features a biomaterial implant into which is incorporated a sustained release polymer containing an anticalcium agent.

In preferred embodiments, the biomaterial implant is, e.g., a bioprosthetic cardiac valve (BCV); the sustained release polymer is a biocompatible polymer which is insoluble in biological fluids, e.g., ethylene-vinyl acetate copolymer; the anticalcium agent is capable of binding to hydroxyapatite crystals, e.g., ethanehydroxydiphosphonate (EHDP); reacting with calcium ions, e.g., EDTA; or reacting with the free aldehyde groups of glutaraldehyde-stabilized bioprosthetics, e.g., aminopropanediphosphonate (APDP); and the polymer is capable of delivering at least 0.5 μg of the anticalcifying agent per 24 hours for a period of at least 5 days.

The treated biomaterial implants of the invention will exhibit substantially increased resistance to pathologic calcification once implanted. They will also avoid the side effects, e.g., growth retardation and calcium imbalance, sometimes associated with anticalcium agents, by administering the agents locally, rather than systemically.

Other features and advantages of the invention will be apparent from the following description of the preferred embodiments thereof, and from the claims.

DESCRIPTION OF THE PREFERRED EMBODIMENTS

We turn now to the structure, manufacture, and operation of preferred embodiments of the invention, first briefly describing the drawings.

DRAWINGS

COMPOSITION OF ANTICALCIFICATION POLYMERS

The biomaterial implants of the invention contain a polymer into which is incorporated an anticalcium agent. Suitable polymers are biocompatible and insoluble in the environment of use. Examples of suitable polymers are acyl substituted cellulose acetates and alkyl derivatives thereof; partially and completely hydrolyzed alkylene-vinyl acetate copolymers; unplasticized polyvinyl chloride; crosslinked homo- and copolymers of vinyl acetate; crosslinked polyesters of acrylic and methacrylate; polyvinyl alkyl ethers; polyvinyl fluoride; silicone; polycarbonate; polyurethane; polyamide; polysulphones; styrene acrylonitrile copolymers; crosslinked poly(ethylene oxide); poly(alkylenes); poly(vinyl imidazole); poly(esters); poly(ethylene terephthalate); and chlorosulphonated polyolefins. These polymers are described in Folkman et al. U.S. Pat. No. 4,378,224, hereby incorporated by reference. Hydrogels, e.g., polyvinylalcohol and poly-2-hydroxy-ethylmethacrylate, can also be used. The most preferred polymer is ethylene-vinyl acetate copolymer.

The anticalcium agent can be any pharmaceutically acceptable compound which inhibits calcification in biological tissue. A number of such compounds are known, e.g., diphosphonate compounds such as ethanehydroxydiphosphonate (EHDP) and aminopropanediphosphonate (APDP), described in Kramsch et al., *Circ. Res.* 42: 562–571, 1978; calcium channel blockers such as nifedipine (Merck Index 10th ed.-#9747) and verapamil (Merck Index 10th ed.-#6374), described in Henry et al., *J. Clin. Invest.* 68: 1366–1369, 1981; calcium chelating agents such as EDTA, described in Wartman et al., *J. Atheroscler. Res.* 7: 331–341, 1967; ionic antagonists such as lanthanum trichloride, described in Kramsch, id.; thiophene compounds, described in Kramsch, id.; and phosphocitrate analogues such as 2-aminotricarballylate. The most preferred anticalcium agent is EHDP.

PREPARATION OF ANTICALCIUM POLYMERS

Generally, the anticalcium polymers are prepared by dissolving the polymer in a suitable solvent and adding the anticalcium compound to the solution. The solution is then added to a biomaterial implant, e.g. by coating the device or by pouring the solution into a hollow portion of the device, after which the solvent is removed in a vacuum oven.

EVA-EHDP

The currently most preferred anticalcium polymer, EVA-EHDP, is prepared as follows: EVA (commercially available) is dissolved as a 10 wt. % solution in methylene chloride. This solution is combined with EHDP in a ratio of one part EHDP per four parts EVA. A typical polymer would contain enough EHDP to deliver 50–75 micrograms of EHDP per 24 hours for between 30 days and 10 years; a typical range of anticalcium agent is 5–50 wt %. The solution is then added to a biomaterial implant and the methylene chloride is removed in a vacuum oven.

STRUCTURE OF THE BIOMATERIAL IMPLANTS

We turn now to a description of the structure and manufacture of preferred biomaterial implants.

BCV

Figure 1:
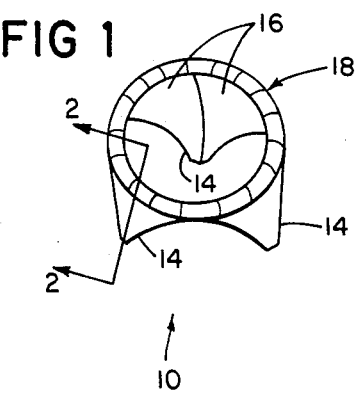
FIG. 1 is a perspective view of a BCV embodying the invention.
Figure 2:
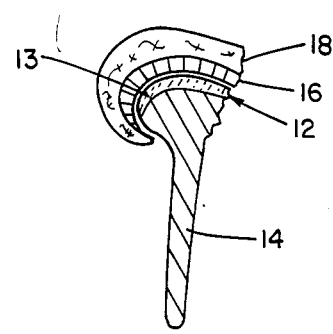
FIG. 2 is a cross-sectional view of the BCV of FIG. 1 taken at 2—2.

There is shown in FIGS. 1 and 2 BCV 10, including mandril 12 bearing a coating 13 of EVA-EHDP. BCV 10 also includes alloy stent 14, porcine aortic cusps 16, and cloth sewing ring 18. Save for the composition of mandril 12, BCV 10 is of conventional structure.

BCV 10 is manufactured by modifying a conventional BCV, typically fabricated from either porcine aortic valves (as in FIG. 1) or bovine pericardium. The previously described solution of EVA and EHDP in methylene chloride is poured into mandril 12 and the methylene chloride is removed in a vacuum oven. BCV 10 is then implanted in the body through open heart surgery.

SYNTHETIC VASCULAR GRAFT

Figure 3:
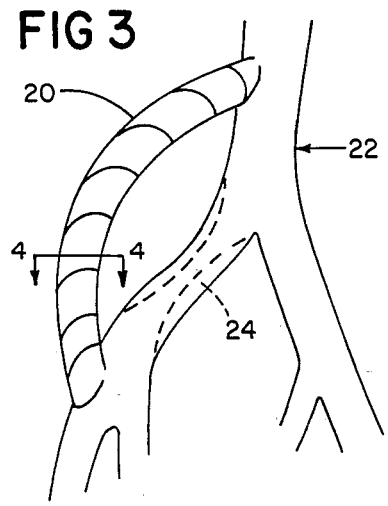
FIG. 3 is a perspective view of a synthetic vascular graft embodying the invention.
Figure 4:
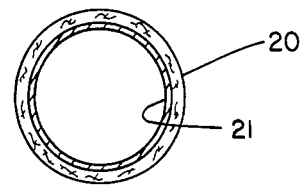
FIG. 4 is a cross-sectional view of the synthetic vascular graft of FIG. 3 taken at 4—4.

FIGS. 3 and 4 show synthetic vascular graft 20 bearing a coating 21 of EVA-EHDP on its inner surface. Graft 20 is attached to peripheral artery 22 in order to bypass arterial occlusive lesions 24.

Vascular graft 20 can be manufactured by overlaying the methylene chloride solution of EVA-EHDP onto the inner surface of a conventional synthetic vascular graft and then removing the methylene chloride in a vacuum oven. Synthetic vascular grafts are typically fabricated from Dacron or Goretex. After treatment the graft can be implanted surgically.

SAPHENOUS BYPASS GRAFT

Figure 6:
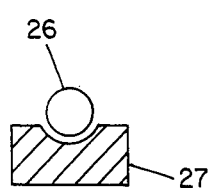
FIG. 6 is a cross-sectional view of the saphenous bypass graft of FIG. 5 taken at 6—6.
Figure 5:
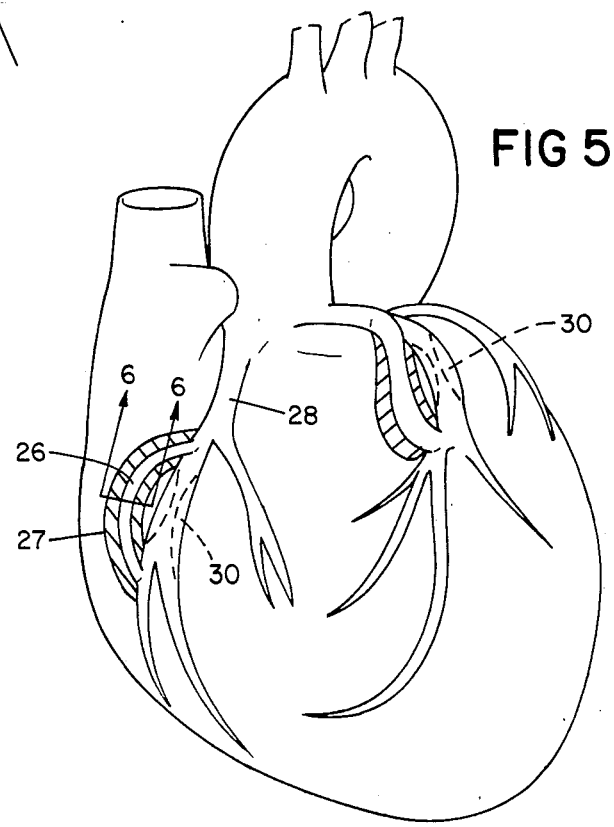
FIG. 5 is a perspective view of a saphenous bypass graft embodying the invention.

FIGS. 5 and 6 show saphenous bypass graft 26 partially encased in an underbedding of EVA-EHDP film 27. Graft 26 is attached to coronary artery 28 in order to bypass arterial occlusive lesions 30.

Saphenous bypass graft 26, an autologous saphenous vein, can be manufactured by casting a thick (approx. 1 mm) film of EVA-EHDP from methylene chloride onto a semi-circular region of the graft surface. Methylene chloride can then be removed in a vacuum oven. Surgical implantation of the treated graft can be accomplished through open heart surgery.

DETACHABLE BALLOON

Figure 7:
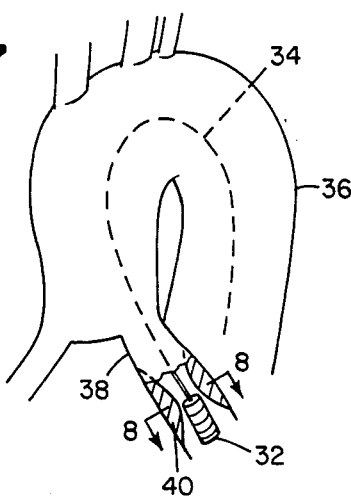
FIG. 7 is a perspective view of a detachable balloon implant on the tip of a cardiac catheter of the invention showing its relationship with cardiac tissue.
Figure 8:
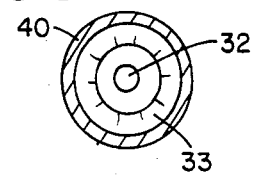
FIG. 8 is a cross-sectional view of a coronary artery containing the detachable balloon of FIG. 7 taken at 8—8.

FIGS. 7 and 8 show detachable balloon 32 coated with EVA-EHDP 33 and affixed to the tip of cardiac catheter 34. Cardiac catheter 34 is inserted through aorta 36 into coronary artery 38 between arterial occlusive lesions 40.

Detachable balloon 32 can be prepared by coating the surface of a conventional detachable cardiac balloon with EVA-EHDP in methylene chloride and then removing the methylene chloride in a vacuum oven. The treated balloon can be placed intra-cardiac, in close proximity to previously implanted bioprosthetics, via cardiac catheterization as shown in FIG. 7.

VENTRICULAR ASSIST DEVICE

Figure 9:
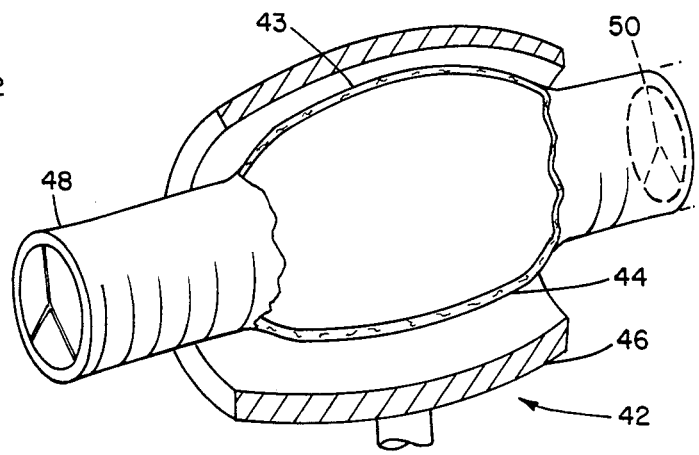
FIG. 9 is a plan view, partially broken away, of a ventricular assist device containing an elastomeric bladder embodying the invention.

There is shown in FIG. 9 ventricular assist device 42 including blood-pumping bladder 44 coated with EVA-EHDP coating 43, encased in pneumatic jacket 46. Blood from the heart enters bladder 44 through inflow valve 48 and exits to the aorta via outflow valve 50.

Ventricular assist device 42 can be manufactured by applying a coating of EVA-EHDP in methylene chloride to the blood-contacting surface of a conventional blood pumping bladder, which is typically composed of an elastomer. After removal of the methylene chloride in a vacuum oven, the treated bladder can be attached to valves 48 and 50, encased in pneumatic jacket 46, and implanted in the body through open heart surgery.

HIP PROSTHESIS

Figure 10:
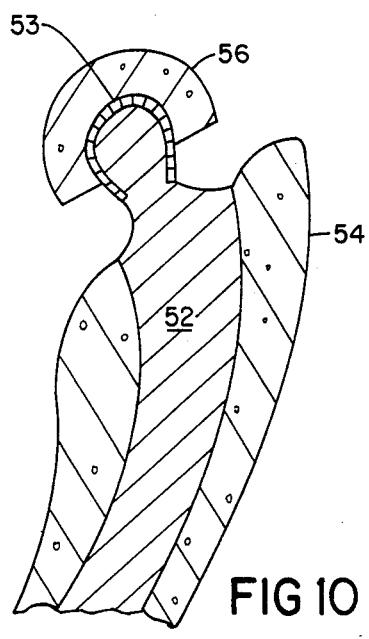
FIG. 10 is a plan view of a hip prosthesis embodying the invention.

FIG. 10 shows hip prosthesis 52 encased in femur 54. The ball joint of hip prosthesis 52 is coated with EVA-EHDP coating 53 and placed in femoral socket 56.

Hip prosthesis 52 can be manufactured by immersing the ball joint of a conventional hip prosthesis in a methylene chloride solution of EVA-EHDP, followed by removal of the methylene chloride in a vacuum oven. After treatment, the hip prosthesis can be surgically implanted.

SILASTIC BREAST IMPLANT

Figure 11:
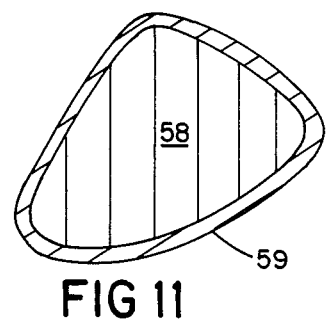
FIG. 11 is a plan view of a silastic breast implant embodying the invention.

In FIG. 11 there is shown silastic breast implant 58 coated with EVA-EHDP coating 59.

Breast implant 58 can be manufactured by dipping a typical silastic breast implant into a methylene chloride solution of EVA-EHDP, and then removing the methylene chloride in a vacuum oven. After treatment, the implant can be placed in the body surgically.

TENDON PROSTHESIS

Figure 12:
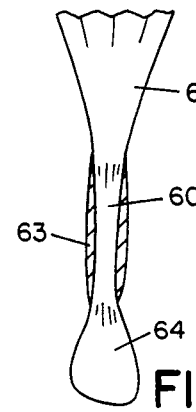
FIG. 12 is a plan view of a tendon prosthesis embodying the invention.

FIG. 12 shows tendon prosthesis 60 having a coating 63 of EVA-EHDP. Tendon prosthesis 60 connects muscle 62 and bone 64.

Tendon prosthesis 60 can be manufactured by immersing a conventional tendon prosthesis in a solution of EVA-EHDP dissolved in methylene chloride. The methylene chloride can be removed in a vacuum oven, after which the treated tendon prosthesis can be surgically implanted.

OPERATION

The biomaterial implants of the invention can be surgically implanted using conventional surgical techniques. Once the device is implanted, the polymeric matrix releases the anticalcium agent at a controlled rate over an extended period of time.

Figure 13:
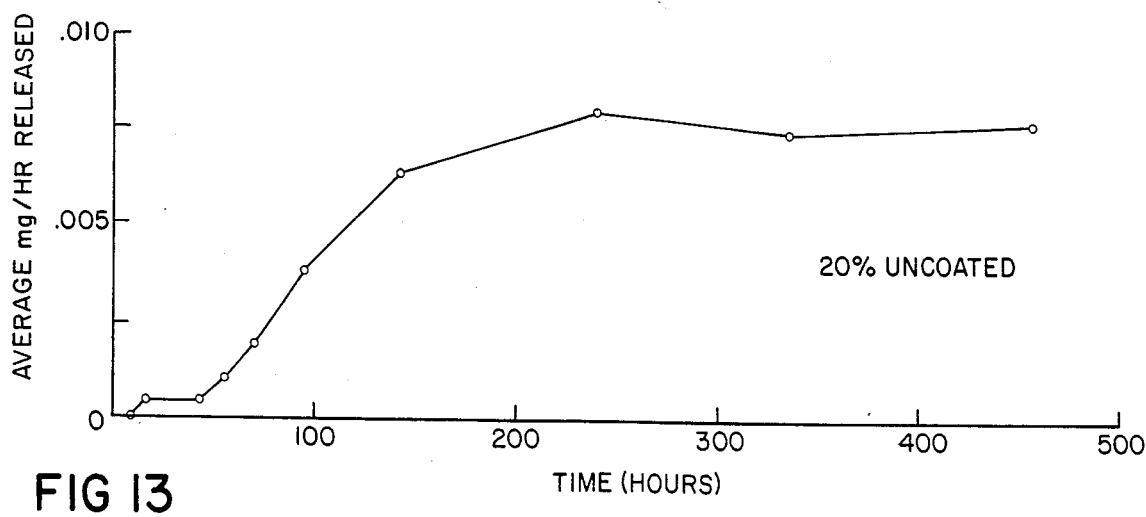
FIG. 13 is a graphical representation of the in vitro release characteristics of EVA-EHDP anticalcium polymer.

FIG. 13 shows the in vitro release characteristics of an EVA-EHDP polymer embodying the invention containing 20 wt. % EHDP. As shown in the graph, after an initial induction period of approximately 150 hrs the rate at which EHDP is released from the EVA matrix is almost constant.

Anticalcium agents generally fall into three classes of compounds. The first class inhibits calcification of both natural and synthetic tissue implants by binding to developing hydroxyapatite crystals associated with calcium mineral salts, thus restricting crystal growth. Diphosphonate compounds such as EHDP and APDP are included in this class.

The anticalcium activity of the second class of compounds is restricted to natural tissue implants such as BCV's fabricated from porcine aortic valves or bovine pericardium. These implants typically are treated with glutaraldehyde to stabilize the tissue via the formation of covalent crosslinks through the aldehyde groups. The crosslinking reaction, however, is incomplete, leaving unreacted aldehyde groups which act as critical sites for calcification. Exposure of the glutaraldehyde stabilized tissue to amino-containing compounds such as APDP (also active in class 1) and 2-aminotricarballylate removes these sites by reacting the amino groups with the aldehydes to form Schiff bases, which are not critical sites for calcification.

The third class of compounds, effective for both natural and synthetic tissue implants, inhibits calcification by removing calcium ions which would otherwise be able to form calcium mineral salt deposits. This class includes calcium chelating agents, e.g., EDTA and 2-aminotricarballylate (also active in class 2); calcium channel blockers, e.g., nifedipine and verapamil; calcium ion antagonists, e.g., lanthanum trichloride; and calcium ligand formers, e.g., thiophene compounds.

The sustained release polymer system will significantly extend the life of natural and synthetic tissue bioprosthetic devices by continuously supplying the anticalcium agent to potential calcification sites. In addition, these devices will avoid the adverse side effects such as growth retardation and calcium imbalance often associated with anticalcium treatment by administering the anticalcium drug locally rather than systemically. This local administration also permits the use of much smaller amounts of anticalcium agents than are needed in systemic intravenous administration.

OTHER EMBODIMENTS

Other embodiments are within the following claims. For example, the anticalcium polymer, rather than being used as a coating, can comprise a structural element in a biomaterial implant.

We claim:

1. A biomaterial implant into which is incorporated a sustained release polymer containing at least one anticalcium agent.

2. The device of claim 1, wherein said polymer is capable of delivering at least 0.5 μg of said anticalcium agent per 24 hours for a period of at least 5 days.

3. The device of claim 1, wherein said anticalcium agent is capable of binding to hydroxyapatite crystals.

4. The device of claim 3, wherein said anticalcium agent comprises a pharmaceutically acceptable diphosphonate.

5. The device of claim 4, wherein said diphosphonate comprises ethanehydroxydiphosphonate (EHDP).

6. The device of claim 4, wherein said diphosphonate comprises aminopropanediphosphonate (APDP).

7. The device of claim 1, wherein said anticalcium agent is capable of reacting with calcium ions.

8. The device of claim 7, wherein said anticalcium agent comprises a pharmaceutically acceptable calcium channel blocker.

9. The device of claim 8, wherein said calcium channel blocker comprises nifedipine.

10. The device of claim 8, wherein said calcium channel blocker comprises verapamil.

11. The device of claim 7, wherein said anticalcium agent comprises a pharmaceutically acceptable calcium chelating agent.

12. The device of claim 11, wherein said calcium chelating agent comprises EDTA.

13. The device of claim 11, wherein said calcium chelating agent comprises a pharmaceutically acceptable phosphocitrate analogue.

14. The device of claim 13, wherein said phosphocitrate analogue comprises 2-aminotricarballylate.

15. The device of claim 7, wherein said anticalcium agent comprises a pharmaceutically acceptable ionic antagonist.

16. The device of claim 15, wherein said ionic antagonist comprises lanthanum trichloride.

17. The device of claim 7, wherein said anticalcium agent comprises a pharmaceutically acceptable calcium ligand former.

18. The device of claim 17, wherein said calcium ligand former comprises a thiophene derivative.

19. The device of claim 1, wherein said anticalcium agent is capable of reacting with the free aldehyde groups of a glutaraldehyde-stabilized biomaterial implant.

20. The device of claim 19, wherein said anticalcium agent comprises pharmaceutically acceptable amino-containing compounds.

21. The device of claim 20, wherein said amino-containing compound comprises aminopropanediphosphonate (APDP).

22. The device of claim 20, wherein said amino-containing compound comprises 2-aminotricarballylate.

23. The device of claim 1, wherein said polymer is a biocompatible polymer which is insoluble in biological fluids.

24. The device of claim 23, wherein said polymer is chosen from a group of natural and synthetic polymers consisting of acyl substituted cellulose acetates and alkyl derivatives thereof; partially and completely hydrolyzed alkylene-vinyl acetate copolymers; unplasticized polyvinyl chloride; crosslinked homo- and copolymers of polyvinyl acetate; crosslinked polyesters of acrylic and methacrylate; polyvinyl alkyl ethers; polyvinyl fluoride; silicone; polycarbonate; polyurethane; polyamide; polysulphones; styrene acrylonitrile copolymers; crosslinked poly(ethylene oxide); poly(alkylenes); poly(vinyl imidazole); poly(esters); poly(ethylene terephthalate); and chlorosulphonated polyolefins; polyvinylalcohol; and poly-2-hydroxy-ethylmethacrylate.

25. The device of claim 24, wherein said polymer comprises ethylene-vinyl acetate copolymer.

26. The device of claim 1, wherein said biomaterial implant is a bioprosthetic cardiac valve.

27. The device of claim 1, wherein said biomaterial implant is a synthetic vascular graft.

28. The device of claim 1, wherein said biomaterial implant is an autologous saphenous bypass graft.

29. The device of claim 1, wherein said biomaterial implant is a detachable cardiac balloon.

30. The device of claim 1, wherein said biomaterial implant is a ventricular assist device containing an elastomeric bladder.

31. The device of claim 1, wherein said biomaterial implant is a hip prosthesis.

32. The device of claim 1, wherein said biomaterial implant is a silastic breast implant.

33. The device of claim 1, wherein said biomaterial implant is a tendon prosthesis.

* * * * *